United States Patent [19]
Quail et al.

[11] Patent Number: 5,656,496
[45] Date of Patent: Aug. 12, 1997

[54] DARK AND LIGHT REGULATED CHLOROPHYLL A/B BINDING PROTEIN PROMOTER/REGULATORY SYSTEM

[75] Inventors: Peter H. Quail, Richmond, Calif.;
Thomas D. Sullivan, Madison, Wis.;
Alan H. Christensen, Albany, Calif.

[73] Assignee: Mycogen Plant Science, Inc., San Diego, Calif.

[21] Appl. No.: 461,082

[22] Filed: Jun. 5, 1995

Related U.S. Application Data

[62] Division of Ser. No. 418,915, Apr. 7, 1995, which is a continuation of Ser. No. 141,411, Oct. 22, 1993, abandoned, which is a continuation of Ser. No. 32,519, Mar. 15, 1993, abandoned, which is a continuation of Ser. No. 574,513, Aug. 28, 1990, abandoned, which is a continuation of Ser. No. 293,684, Jan. 5, 1989, abandoned.

[51] Int. Cl.$^6$ .......................... C12N 15/82; C12N 15/11
[52] U.S. Cl. ........................ 435/320.1; 536/24.1
[58] Field of Search ................. 536/24.1; 435/320.1, 435/172.3; 800/205

[56] References Cited

PUBLICATIONS

Computational Molecular Biology. sources and methods for sequence analysis. (2nd. ed.), Oxford University Press, Oxford, 1988, pp. 170–171.

Cashmore (1984) Proc. Natl. Acad. Sci. 81:2960–2964.
Nelson, et al. (1984) J. Cell. Biol. 98:558–564.
Sheen and Bogard (1986) Proc. Natl. Acad. Sci. 83:7811–7815.
Simpson, et al. (1985) EMBO J. 4:2723–2729.
An (1987) Mol. Gen. Genet. 207:210–216.
Lamppa, et al. (1985) Nature 316:750–752.
Sullivan, et al. (1989) Mol. Green. Genet. 215:431–440.
Shimamoto, et al. (1989) Nature 338:274–276.
Sheen, et al. (1986) Proc. National Academy of Science 83: 7811–7815.
Frischauf, et al. (1983) J. Mol. Biol. 170: 827–842.
Horn, et al. (1988) Plant Cell Reports 7: 469–472.
Gelvin (1987) Plant Molecular Biology 8:355–359.
An (1987) Mol Gen. Genet. 207: 210–216.

*Primary Examiner*—Che S. Chereskin
*Attorney, Agent, or Firm*—Saliwanchik, Lloyd & Saliwanchik

[57] ABSTRACT

A dark- and light-regulated chlorophyll a/b (Cab) binding protein promoter/regulatory system from maize is disclosed. This promoter/regulatory system is capable of accounting for as much as 80% of the total Cab mRNA in the dark and results in enhancement of expression from 3- to 6-fold after conditions of illumination. This Cab promoter/regulatory system may be recombined with structural genes for expression in plant cells.

4 Claims, 4 Drawing Sheets

FIG. 2A

```
EcoRI
GAATTCACGGAAGATCTCGAGACTAGGAGACGGAACGCGCGATGGGAGGGGCGGGCGCTGACCTTTCTGGCGAGTCGAGG    -740
                                                                                •
TAGCGGTAGAGCAGCTGCAGCCGCGGACACGATGAGGAAGACGAAGATAGCCGCCAGGACATGTCGCCGGCGGAGGCTGAGCCGGTCTC    -640
                                                                                •
TCCGGCCTCCGATCGGCGTTAAGTTGGGATCGTAACGTGACGTGTCTCCTCCACAGATCGACACAACCGGCCACTCGGTGCACGACGCCGACA    -540
                                                                                •
AGGGTGAGATGTCCGTGCACGCAGCCCGTTTGGAGTCTCGTTGCCCACGAACGACCCCTTACGAACAAGGCCTAGCCCAAAACTATTCTGAGTTGAG    -440
                                                                                •
CTTTTGAGCCTAGCCACCTAAGCCGAGCGTCATGAACTGATGAACCCACTACCACTAGTCAAGGCAAACCACAACCACAAATGATCAATTGATCTAGA    -340
                                                                                •
ACAATCCGAAGGAGGCCACGTCACACTCACACCAACCGAAATATCTGCCAGTATCAGATCAACCGGCCAATAGGACGCCAGCGAGCCAACACCT    -240
                                                                                •
AGCGACGCCGCAAAATTCACCGCGAGGGGCACGGGCAAAACAAAAGCCCGGCGGTGAGAATATCTGGCGACTGGCGGAGACCTGGTGGCCA    -140
                                                                                •
                                                                  PvuI
GCGGCGCGGCCCACATCAGCCACACCCCATTCCGCCAGCCAATGGCAACTCGTCTTAAGATTCCACGAGATAAGGACCGATCGCCGGC    -40
                                         +1
                                         ***
GACGCTATTTAGCCAGGTGTGCGCCCCCCACGGTACACTCCACCAGCGCATCTATAGCAACCGGTCCAACACTTTCAGCTTCAGCTTCAGCAATGGCTGCC    61
                                                                  ▼        M  A  A
                                                                                •
TCCACCATGGCGATCTCCTCACGGCGATGGCCGGCACCCCATCAAGGTGGGTTCCTTCGGCGAGGCCGCATCACCATGCGCAAGACCGTGGGCAAGC    161
 S  T  M  A  I  S  S  T  A  M  A  G  T  P  I  K  V  G  S  F  G  E  G  R  I  T  M  R  K  T  V  G  K  P
NcoI
CCAAGGTGCGCCGTCCGGCAGCCCTGGTACGCCCCGACCGCGTCAAGTACCTCGGCCCCCTTCTCCGGCGAGCCCGAGCTACCTCACCGGCGAGTT    261
 K  V  A  A  S  G  S  P  W  Y  G  P  D  R  V  K  Y  L  G  P  F  S  G  E  P  P  S  Y  L  T  G  E  F
                                                                                •
CCCCGGCGACTACGGCTGGGACACCGCCGGCCTGTCCGCCGAGACCATTCGCCAAGAACCGCGAGCTGGAGGTGATCCACTCCCGCTGGGCCATG    361
 P  G  D  Y  G  W  D  T  A  G  L  S  A  D  P  E  T  F  F  A  K  N  R  E  L  E  V  I  H  S  R  W  A  M
```

FIG. 2B

```
CTCGGCGCGCTCGGCTGCGTCTTCCCCGAGCTGCTCTCCCGCAACGGCGTCAAGTTCGGCGAGGCCGTCGTTGGTTCAAGGCCGGCTCCCAGATCTTCAGCG    461
 L  G  A  L  G  C  V  F  F  P  E  L  L  S  R  H  G  V  K  F  G  E  A  V  W  F  K  A  G  S  Q  I  F  S  E

AGGGCGGGCTGGACTACCTCGGCAACCCCAGCTTGATCCACGCGCAGAGCATCCTCGCCATCTGGGCCTGTCAGGTCGTGCTCATGGGTGCCGTCGAGGG    561
 G  G  L  D  Y  L  G  N  P  S  L  I  H  A  Q  S  I  L  A  I  W  A  C  Q  V  V  L  M  G  A  V  E  G

CTACCGCATTGCCGGCGGCCCTCGGCGAGGTCGTCGACCCCTGTACCCTGGCGGCAGCTTCGACCCCCTCGGCCTGGCCGACGACCCCGAGGCCTTC    661
 Y  R  I  A  G  G  P  L  G  E  V  V  D  P  L  Y  P  G  G  S  F  D  P  L  G  L  A  D  D  P  E  A  F

GCCGAGCTCAAGGTGAAGGAGCTCAAGAACGGCCGCCTCGCCATGTTTTCCATGTTCGGCTTCTTCGTCCAGGCCATCGTCACCGGCAAGGGCCCGCTCG    761
 A  E  L  K  V  K  E  L  K  N  G  R  L  A  M  F  S  M  F  G  F  F  V  Q  A  I  V  T  G  K  G  P  L  E
                          ↓λJ8                                                                  NciI

AGAACCTCGCTGACCACATCGCTGACCCAGTCAACAACAACGCCATGGCCTACGCCACCAACTTCGTCCCCGGCAACTAAGCTCAACGGCTATGCTATGC    861
 N  L  A  D  H  I  A  D  P  V  N  N  N  A  W  A  Y  A  T  N  F  V  P  G  N  *
                                                                         NsiI

AACTTCATTGTCTTTCGGATCGGAGAGGTGTACGTGGATTGATTGATGCTGTGGATGCATGTGTCTTTTGTTCACGTTGCATTGCATAGGC    961

AAGTCGAGATGATGAGTTGGCGTTGTACACTAAGATGAACCATGTTGTGCAATAGTGGTGGTTTTGTTTCCTGCTGGTTAATTGTTGATATCCATTAA    1061
                                                (A)          (B)       (C)
                                               *****          ***     EcoRV ***

TTTGTTTTTCTCTATACTCCTTTTTCTCTCTAGCTCTTTTATCTTAAGAAGGCAAGCATAAATGTGCTTGGATAAACAGCAGATAAATCAATGAAAATGAAA    1161
    (D)                                                                              ↓λK20(HindIII)
   ****

GTAGTCTTATACCATTTAAATGTGGGCAAACAAATAAGATATGCACTTAAACAGTAACGAACGAATCTAGAGAAAATAGAAAGAGGGTATACTTGTCTTA    1261
```

DARK AND LIGHT REGULATED CHLOROPHYLL A/B BINDING PROTEIN PROMOTER/REGULATORY SYSTEM

This application is a divisional application of Ser. No. 08/418,915, filed Apr. 7, 1995; which is a continuation application of Ser. No. 08/141,411, filed Oct. 22, 1993 now abandoned; which is a continuation application of Ser. No. 08/032,519, filed Mar. 15, 1993 now abandoned; which is a continuation of application Ser. No. 07/574,513, filed Aug. 28, 1990 now abandoned; and which is a continuation application of Ser. No. 07/293,684, originally filed Jan. 5, 1989 now abandoned.

FIELD OF THE INVENTION

This invention is in the area of plant molecular biology and concerns gene expression in plant hosts. This invention describes the identification and characterization of a sequence of DNA from the upstream nontranscribed region of a plant chlorophyll a/b binding (Cab) protein gene. This novel nucleotide sequence is capable of initiating and driving the transcription of nearby, preferably downstream, plant expressible genes in a constitutive and light-regulated manner. This invention will enable the selective expression and regulation of desired structural genes in plant tissues under conditions of light or darkness.

BACKGROUND OF THE INVENTION

In most plants a wide variety of physiological processes are influenced by light acting through one or more photoreceptors. Phytochrome, one of the best characterized photoreceptors, is a chromoprotein that exists in either of two spectrally distinct and photointerconvertible forms: $P_r$ and $P_{fr}$. $P_{fr}$ is the biologically active form of the molecule. $P_r$ is converted to $P_{fr}$ by red light which then induces physiological responses; far-red light, which drives $P_{fr}$ back to $P_r$, will usually negate the inductive effect of red light, if it is given sufficiently soon after the red. Inductions by small amounts of red light and reversibility with far-red light are standard criteria by which phytochrome involvement in a process is assessed (Shropshire and Mohr, (eds.) (1983) Photomorphogenesis, Encyc. Plant Physiol. 16:3–19).

Many of the physiological responses to light involve changes in gene activity; different RNA sequences are synthesized when dark-grown plants are transferred to light. Responses of a given gene to light may not always be the same in different plants. There is considerable diversity of responses for different genes and for the same gene under different physiological conditions. For example, it has been shown that the mRNA level of the ribulose-1,5-bisphosphate carboxylase, small subunit (rbvcS) gene may be very high in several plant species (peas, tobacco, maize) yet quite low in others (barley, mungbean) (Tobin and Silverthorne (1985) Ann. Rev. Plant. Physiol. 36:569–593). Also, the contribution to total mRNA by different members of a gene family may be variable and may be influenced by light (Kaufman et al. (1985) Plant Physiol. 78:388–393). The molecular basis for such differential responsiveness remains unknown.

It is generally believed that there are specific DNA sequences which can confer light responsiveness on a gene and which can determine the various different patterns of light induction. The most abundant mRNAs in leaves of higher plants encode the chlorophyll a/b binding (Cab) protein and the rbcS. Nuclear genes for these mRNAs are expressed in an organ-specific manner and their expression is induced by light acting through phytochrome.

Cab proteins associate with chlorophylis a and b to form the light harvesting complex which absorbs energy from light and transfers the resultant excitation energy to photosystems I and II (Arntzen (1978) Curr. Top. Bioenerget. 8:111–160). The Cab proteins are synthesized by free cytoplasmic ribosomes as precursor proteins, which contain an amino acid terminal extension or transit peptide. This transit peptide is cleaved during membrane translocation to produce the mature polypeptide (Schmidt et al. (1981) J. Cell. Biol. 91:468–478).

Cab proteins are encoded by small gene families as part of the nuclear genome in several plant species (Dunsmuir (1985) Nucl. Acid Res. 13:2503–2518). Polypeptides of different sizes appear to be encoded by these genes.

To investigate the regulation and expression of Cab genes in more detail, Lamppa et al. (1985) Mol. Cell. Biol. 5:1370–1378, sequenced a genomic clone for a major Cab polypeptide from wheat. This gene encoded a 70 nucleotide 5'-nontranslated spacer, a 34 amino acid transit peptide and a mature coding protein of 232 amino acid residues. The molecular weight of the precursor polypeptide was 28,560 daltons. The wheat Cab gene structure was compared with that of a cab gene from pea (Cashmore (1984) Proc. Natl. Acad. Sci. 81:2960–2964). The coding regions of genomic clones from pea (dicot) and wheat (monocot) showed 90% homology, whereas the wheat transit peptide was 3 amino acids shorter than that found in pea. Furthermore, within the various Cab genes, sequence divergence was observed in the 5'-nontranslated leader region as well as in the transit peptide.

The schedule of expression for Cab mRNAs and polypeptides during maize leaf development in light and darkness was determined by Nelson et al. (1984) J. Cell. Biol. 98:558–564. In maize, Cab polypeptides increased during development in light from very low or undetectable levels to become one of the most abundant leaf proteins. In this study it was found that the maize Cab protein accumulation was absolutely dependent on light and only low levels (<0.5% of final levels) of Cab mRNA could be detected in dark-grown tissue, but these mRNA levels increased up to 200 fold with illumination. In many other plants the same overall result was obtained—that the expression of Cab gene is regulated by light, with little or none of the pre-Cab mRNA being present in dark-grown tissue (Cashmore (1984) supra).

The maize Cab multigene family is thought to consist of at least 12 members (Sheen and Bogorad (1986) Proc. Natl. Acad. Sci. 83:7811–7815). Six members of the maize Cab multigene family were identified and studied selectively for expression patterns (Sheen and Bogorad (1986) supra). In cells of illuminated dark-grown maize leaves, transcripts of these six Cab genes were present at vastly different levels and accounted for about 95% of total Cab mRNA. After 24 hours of greening, Cab-m1 was the most highly expressed gene, contributing approximately 30% of the total Cab mRNA; while Cab-m5, Cab-m2, Cab-m3, Cab-m4, and Cab-m6 contributed 20%, 18%, 15%, 8% and 4%, respectively. Of these six maize Cab genes, Cab-m1, the most highly expressed gene of the family in greening leaves, and Cab-m6, the least expressed, were both strongly induced by light. Cab-m5 was induced by light less strongly, whereas Cab-m2, Cab-m3 and Cab-m4 were induced by light only slightly. mRNAs of two Cab genes (Cab-m4, and to a lesser extent Cab-m3), were present in etiolated seedlings prior to illumination and did not show strong light responsiveness.

The studies of Sheen and Bogorad (1986) supra can be compared to those of Nelson et al. (1984) supra. In showing that accumulation of Cab polypeptides in whole maize leaves was absolutely light-dependent while the mRNA, present at a low level in the dark was dramatically stimulated by light, Nelson et al. (1984) supra may have described the expression patterns of the Cab-m1 and Cab-m6 genes of illuminated dark-grown maize seedlings as reported by Sheen and Bogorad (1986) supra. The other four Cab genes described by Sheen and Bogorad (1986) supra did not show such dramatic response to light. These studies of Sheen and Bogorad (1986) supra suggested that the six members of the maize multigene family are not regulated through a common mechanism. Whether the various Cab proteins encoded by the different genes and under different regulatory controls have different functions or whether the proteins are interchangeable is not known.

The regulatory functions of the 5'-flanking sequences of the pea Cab gene were investigated by Simpson et al. (1985) EMBO J. 4:2723–2729. Two fragments containing either 2.5 or 0.4 kbp of the 5' flanking sequences upstream to the transcription start site of the pea Cab gene were fused to the neomycin phosphotransferase II (NPT(II)) gene from Tn5 as an enzymatic reporter. It was shown that 0.4 kbp of the upstream flanking sequences of the pea Cab gene were sufficient for both organ-specific and light-regulated expression of the chimeric constructs in transformed tobacco plants. In addition, it was shown in this study that sequences further upstream (–2.5 to –0.4 kbp from the transcription start site) are required for enhancement (regulation) of the overall level of expression. However, when the 5'-flanking sequences of the Cab gene were replaced with the nopaline synthase (nos) promoter (the nos promoter is known to be constitutively expressed in all tissues of transformed plants but is not normally photoresponsive), the level of NPT(II) activity in the transgenic plants was no longer light responsive. These observations indicated that: (a) DNA sequences important in defining light/dark differences are located in the 5' flanking region, although intragenic or 3' sequences may also have important roles in regulating gene function, and (b) control is at the transcriptional level.

Continuing work on the 5' flanking sequences of the pea Cab gene revealed the presence of an enhancer-like element in the upstream region within 400 bp of the transcription start site (Simpson et al. (1986) Nature 323:551–554). The enhancer activity was found to reside within a 247 bp fragment from –100 to –347 bp in the 5' flanking region of the AB80 gene. This 247 bp sequence was cloned in both orientations upstream of the constitutively expressed nos promoter and fused to the NPT coding sequence. In control constructs devoid of the 247 bp sequence, transgenic plants were unresponsive to light conditions. In contrast, when the 247 bp sequence was inserted in either direction into fusion constructs, the resultant transgenic plants showed four to eight times higher NPT activity under light than under dark growth conditions. These experiments showed that the presence of the pea AB80 upstream element confers light-inducible properties on the recombinant nos/NPT gene and, in addition, showed that insertion of two copies of the upstream element 5' to the nos promoter appeared to have an additive effect.

Other work by Nagy et al. (1986) Phil. Trans. R. Soc. Lond. 314:493–500) with the Cab gene from wheat suggested that an important cis-acting regulatory element was located between –90 and –144 of the Cab-1 gene. These authors also suggested that by analogy with other regulated genes, the Cab upstream segment contained one or more light responsive elements comprising the 'GT' sequence motif resembling the SV40 enhancer core Sequence (Gluzman (1983) in *Enhancers and eukaryotic gene expression*, Y. Gluzman (ed.) Cold Spring Harbor, N.Y., pp. 27–32) to which cognate transacting factors would bind.

SUMMARY OF THE INVENTION

The primary object of this invention is to provide novel DNA segments comprising a transcriptional regulatory system recognized by plant hosts. The regulatory functions of this DNA fragment from the upstream region of a plant photosynthetic gene are unique in that they comprise unexpectedly active regulation of constitutive expression under conditions of complete darkness as well as light-induced regulation and enhancement of gene expression. This invention enables those skilled in the art to selectively and actively express—under dark or light conditions—desired structural genes in plant tissue. The promoter system comprises the DNA sequences from the 5' untranscribed regions of plant Cab genes that initiate and regulate—under dark and under light conditions—the transcription of genes placed under its control. In its preferred embodiment, the promoter sequence is derived from the upstream region of a Cab gene from maize that functions actively in the dark and that is also light-inducible.

This invention also comprises the first report of an isolated maize Cab gene. The present work describes the isolation and characterization of a promoter which is active in plants to control and regulate the expression of a downstream structural gene. This DNA sequence is found as a naturally-occurring, untranscribed region upstream of the Cab AB1084 structural gene isolated from a maize genomic library. The transcription start site or cap site, as determined by S1 nuclease mapping, is designated as base 1, and the sequences embodied within about 840 bases 5' of the transcription start site, plus about 54 nucleotides 3' of the cap site, but 5' of the translation start site, constitute the Cab promoter. Located within this approximately 0.9 kb promoter region are a TATA box at 35 nt, a CAAT box at –90 nt and activating elements that respond to stimuli such as light.

A further object of this invention is to provide a means for obtaining active gene expression in plants grown in the dark. The promoter system of the maize genomic Cab gene described in the present invention is unexpectedly active in maize leaves grown in the dark. This novel result enables the creation of recombinant DNA molecules comprising a dark- and light-active, plant-expressible promoter and a plant-expressible structural gene, wherein the structural gene is placed under the regulatory control of all transcription initiating and activating elements of the promoter. In particular, the plant Cab promoter can be combined with a variety of DNA sequences, typically structural genes, to provide DNA constructions for regulated expression of said DNA sequences under conditions of darkness. The extent of expression and regulation by the Cab gene promoter of this invention under conditions of total darkness represents a novel regulatory system within this Cab gene that is distinct from that of other known maize Cab gene promoters.

Additionally, this invention provides a means for enhancing the level of gene expression obtained in dark-grown plants. The Cab promoter as described in this invention exhibits enhanced levels of gene expression under conditions of light. This invention allows formulation of recombinant DNA molecules wherein a plant expressible structural gene is placed under the regulatory control of all transcription initiating and activating elements of said promoter. DNA constructions in which the Cab promoter is combined with plant-expressible structural genes allow light-induced, dark-active, promoter-regulated expression of the desired protein.

This invention is particularly useful for efficacious expression of photoregulated genes. Whereas in expression systems utilizing constitutive promoters under conditions of darkness, protein synthesis is susceptible to feedback regulation, in expression systems utilizing dark- and light-active promoters, a mechanism exists for more sustained protein synthesis. Under conditions of darkness, transcripts of photoregulated genes are accumulated and upon subsequent illumination, light-induced translation of accumulated transcripts results in more efficient gene expression and thereby allows more efficient organization of specialized proteins into photoregulated complexes.

BRIEF DESCRIPTION OF THE FIGURES

FIGS. 2A and 2B document the sequence of AB1084 transcribed region plus flanking DNA. The CAP site is denoted as base +1. The deduced amino acid sequence is shown below the nucleotide sequence starting at +53. The start site of the mature peptide is indicated by a filled triangle; (A), (B), (C) and (D) mark sites of 3' termini found in AB1084 mRNA's. Boxed sequences include a "CAAT" box at −90, a "TATA" box at −35, putative polyA addition signals at +999, +1057 and +1119. The amino acid sequences with homology to consensus transit peptide for Cab proteins are also boxed. The site of polyA in cDNA clone AB1084 is indicated at +1033. Restriction enzyme sites used in subcloning, probe preparation and for SP6 transcription are shown. ΔJ8 and ΔK20 mark the 3' end points of deletion clones used for probe preparation and SP6 transcription.

FIG. 1) was hybridized in hybridization buffer with 30% formamide and washed with wash buffer containing 2× SSC at 42° C. SSC is a standard buffer containing 150 mM NaCl and 15 mM Na citrate. (B) The 3'-untranslated region probe (ΔK20, NciI; FIG. 1) was hybridized in buffer containing 50% formamide and washed with wash buffer containing 0.1× SSC at 65° C. Autoradiography was for 11 hours at room temperature. Brome mosaic virus RNA was used as molecular size markers as indicated on the right. The size of the SP6/Cab transcript (1.3 kbp) is also indicated on the right.

DETAILED DESCRIPTION OF THE INVENTION

Figure 1:
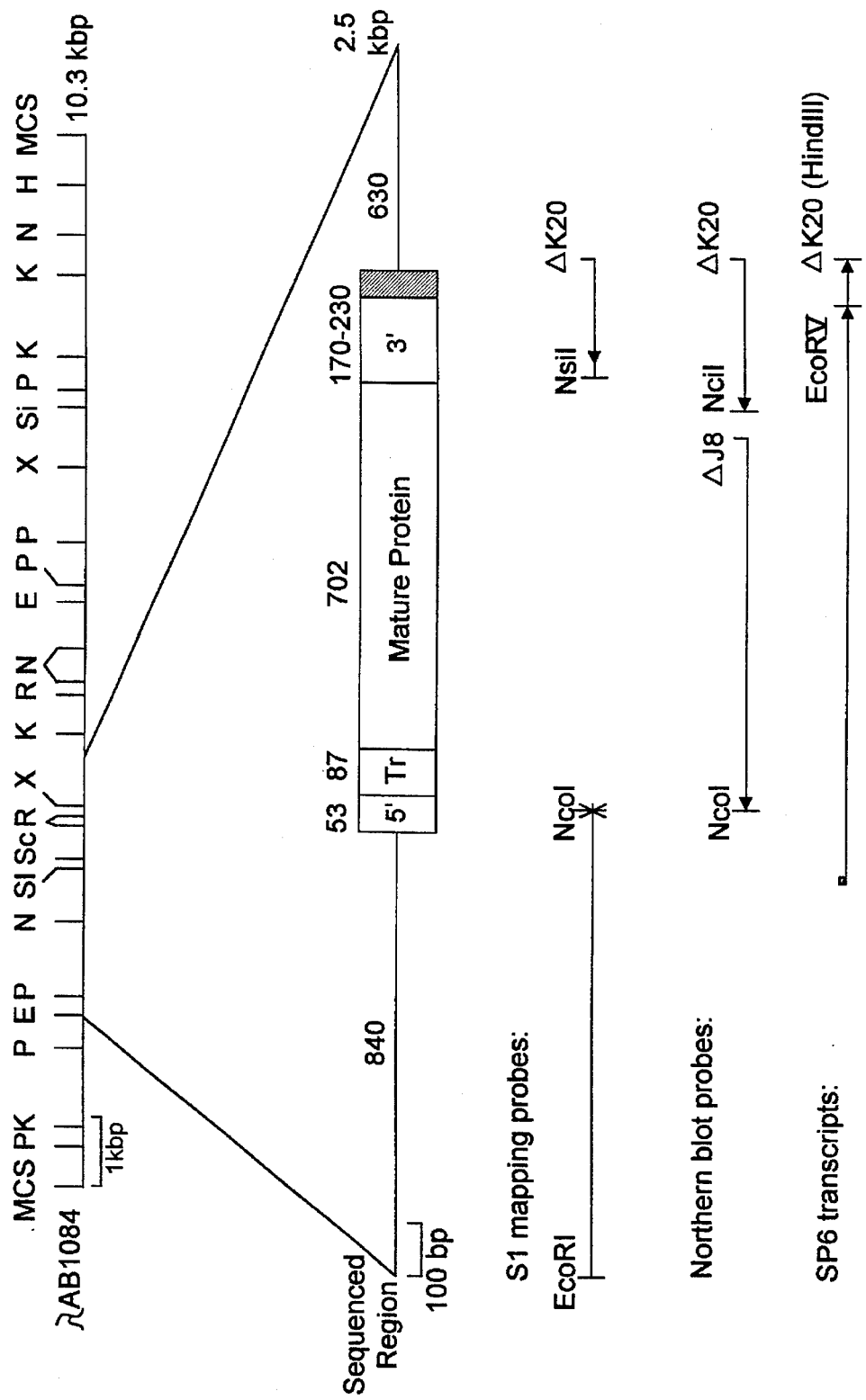
FIG. 1 is a map of maize gene clone λAB1084 indicating restriction fragments used for transcript analysis. The top line shows the restriction enzyme map of the entire 10.3 kbp Cab gene insert: MCS, multiple cloning site of λphage charon 35; P, PstI; K, KpnI; E, EcoRI; N, NcoI; SI, SalI; Sc, SacI; R, EcoRV; X, XbaI; H, HindIII. The second line shows a summary of the sequenced region including the block indicating the transcribed region of the gene: 5',5'-untranslated region of mRNA; Tr, region encoding the transit peptide; 3',3'-untranslated region of mRNA. The hatched region represents the 60 nucleotide region where several 3' termini are found in the transcribed mRNA. The numbers above the boxes are the length in bp. The various restriction fragments from subclones of λAB1084 that were used in the RNA analyses are shown below: ΔJ8 and ΔK20 are the end points of deletion subclones.

The following definitions are provided in order to remove ambiguities as to the intent or scope of their usage in the specification and claims.

Expression refers to the transcription and/or translation of a structural gene.

Promoter refers to the nucleotide sequences at the 5' end of a structural gene which direct the initiation of transcription. Promoter sequences are necessary, but not always sufficient, to drive the expression of a downstream gene. In general, eukaryotic promoters include a characteristic DNA sequence homologous to the consensus 5'-TATAAT-3' (TATA) box about 10–30 bp 5' to the transcription start site (CAP) site, which, by convention, is numbered +1. Bases 3' to the cap site are given positive numbers, whereas bases 5' to the cap site receive negative numbers, reflecting their distance from the cap site. Another promoter component, the CAAT box, is often found about 30 to 70 bp 5' to the TATA box and has homology to the canonical form 5'-CCAAT-3' (Breathnach, R. and Chambon, P. (1981) Ann. Rev. Biochem. 50:349–383). In plants the CAAT box is sometimes replaced by a sequence known as the AGGA, a region having adenine residues symmetrically flanking the triplet G(orT)NG (Messing, J. et al. (1983) in *Genetic Engineering of Plants*, T. Kosuge et al. (eds.) Plenum Press, pp. 211–227). Other sequences conferring regulatory influences on transcription can be found within the promoter region and extending as far as 1000 bp or more from the cap site.

Regulatory Control refers to the modulation of gene expression induced by DNA sequence elements located primarily, but not exclusively, upstream of (5' to) the transcription start site. Regulation may result in an all-or-nothing response to environmental stimuli, or it may result in variations in the level of gene expression. In this invention, regulatory elements function to enhance the level of downstream gene expression in response to light.

Placing a structural gene under the regulatory control of a promoter or a regulatory element means positioning the structural gene such that the expression of the gene is controlled by these sequences. In general, promoters are found positioned 5' (upstream) to the genes that they control. Thus, in the construction of heterologous promoter/structural gene combinations, the promoter is preferably positioned upstream to the gene and at a distance from the transcription start site that approximates the distance between the promoter and the gene it controls in its natural setting. As is known in the art, some variation in this distance can be tolerated without loss of promoter function. Similarly, the preferred positioning of a regulatory element with respect to a heterologous gene placed under its control reflects its natural position relative to the structural gene it naturally regulates. Again, as is known in the art, some variation in this distance can be accommodated.

Promoter function during expression of a structural gene under its regulatory control can be tested at the transcriptional stage using DNA-RNA hybridization assays and at the translational stage using specific functional assays for the protein synthesized (for example, enzymatic activity).

Structural gene is that portion of a gene comprising a DNA segment encoding a protein, polypeptide or a portion thereof, and excluding the 5' sequence which drives the initiation of transcription. The structural gene may be one which is normally found in the cell or one which is not normally found in the cellular location wherein it is introduced, in which case it is termed a heterologous gene. A heterologous gene may be derived in whole or in part from any source know to the art, including a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bound by the appropriate splice junctions. The structural gene may be a composite of segments derived from a plurality of sources, naturally occurring or synthetic. The structural gene may also encode a fusion protein. It is contemplated that the introduction into plant tissue of recombinant DNA molecules containing the promoter/ structural gene/polyadenylation signal complex will include constructions wherein the structural gene and its promoter are each derived from different plant species.

Plant Dark- and Light-Active Cab Promoter/Regulatory System refers to the approximately 1.0 kbp, and preferably 0.9 kbp, nucleotide sequence 5' to the translation start site of a plant Cab gene, and preferably a maize Cab gene, and more preferably the maize Cab AB1084 gene, and comprises sequences that under conditions of darkness and of light direct initiation of transcription, regulations of transcription, control of expression level, induction of photosynthetic genes and exhibit light induced enhancement of gene expression obtained in the dark. The regulatory system, comprising both promoter and regulatory functions, is the DNA sequence providing regulatory control or modulation of gene expression. Sequences having approximately 85% homology to the maize Cab AB1084 gene are considered to be equivalent and the term, plant dark- and light-active Cab promoter/regulatory system, is meant to encompass sequence equivalents. A structural gene placed under the regulatory control of the plant Cab regulatory system means that a structural gene is positioned such that the regulated expression of the gene is controlled by the sequences comprising the Cab regulatory system. Any plant-expressible structural gene can be employed; the nopeline synthase structural gene is utilized as an example, but as is well-known in the art, other structural genes will work as well.

Enhancer refers to a eukaryotic promoter sequence element that appears to increase transcriptional efficiency in a manner relatively independent of position and orientation with respect to a nearby gene (Khoury and Gruss (1983) Cell 33:313–314). The ability of enhancer sequences to function upstream from, within or downstream from eukaryotic genes distinguishes them from classic promoter elements. The prototype enhancer, the 72 bp tandem repeat of SV40 DNA, contains a "core" sequence, GGTGTGGAAAG, which was shown to be essential to SV40 enhancer function. Morelli et al. (1985) Nature 315:200–204, reported a control sequence for dicot light-regulated genes, which is 5'-CATTATATATAGC(orA)-3'.

Polyadenylation signal refers to any nucleic acid sequence capable of effecting mRNA processing, usually characterized by the addition of polyadenylic acid tracts to the 3'-ends of the mRNA precursors. The polyadenylation signal DNA segment may itself be a composite of segments derived from several sources, naturally occurring or synthetic, and may be from a genomic DNA or an mRNA-derived cDNA. Polyadenylation signals are commonly recognized by the presence of homology to the canonical form 5'-AATAA-3', although variation of distance, partial "readthrough," and multiple tandem canonical sequences are not uncommon (Messing, J. et al. supra). It should be recognized that a canonical "polyadenylation signal" may in fact cause transcriptional termination and not polyadenylation per se (Montell, C. et al. (1983) Nature 305:600–605).

Plant tissue includes differentiated and undifferentiated tissues of plants including, but not limited to, roots, shoots, leaves, pollen, seeds, tumor tissue and various forms of cells in culture, such as single cells, protoplasts, embryos and callus tissue. The plant tissue may be in planta or in organ, tissue or cell culture.

Photoregulation refers to the regulatory response to a light stimulus of a system, for example, in photosynthesis or in developmental and regulatory mechanisms.

Conditions of darkness refers to conditions under which dark-grown plants are maintained and harvested without safelights to avoid low fluence light effects.

Homology, as used herein, refers to identity or near identity of nucleotide and/or amino acid sequences. As is understood in the art, nucleotide mismatches can occur at the third or wobble base in the codon without causing amino acid substitutions in the final polypeptide sequence. Also, minor nucleotide modifications (e.g., substitutions, insertions or deletions) in certain regions of the gene sequence can be tolerated and considered insignificant whenever such modifications result in changes in amino acid sequence that do not alter the functionality of the final product. It has been shown that chemically synthesized copies of whole, or parts of, gene sequences can replace the corresponding regions in the natural gene without loss of gene function. Homologs of specific DNA sequences may be identified by those skilled in the art using the test of cross-hybridization of nucleic acids under conditions of stringency as is well understood in the art (as described in Hames and Higgins (eds.) (1985) *Nucleic Acid Hybridisation*, IRL Press, Oxford, UK). Extent of homology is often measured in terms of percentage of identity between the sequences compared. Thus, in this disclosure it will be understood that minor sequence variation can exist within homologous sequences.

Derived from is used herein to mean taken, obtained, received, traced, replicated or descended from a source (chemical and/or biological). A derivative may be produced by chemical or biological manipulation (including but not limited to substitution, addition, insertion, deletion, extraction, isolation, mutation and replication) of the original source.

Chemically synthesized, as related to a sequence of DNA, means that the component nucleotides were assembled in vitro. Manual chemical synthesis of DNA may be accomplished using well established procedures (Caruthers, M. (1983) in *Methodology of DNA and RNA Sequencing*, Chapter 1, Weissman (ed.), Praeger Publishers, New York), or automated chemical synthesis can be performed using one of a number of commercially-available machines.

Leader sequence refers to a DNA sequence comprising about 100 nucleotides located between the transcription start site and the translation start site. Embodied within the leader sequence is a region that specifies the ribosome binding site.

The present invention is novel DNA comprising promoter and regulatory functions that normally control the natural expression of a Cab gene in maize leaves. Gene expression under control of this promoter/regulatory sequence is light-inducible and, in addition, occurs constitutively in darkness. The invention further comprises the aforementioned DNA ligated with a plant-expressible structural gene and also recombinant vectors comprising the aforementioned DNA/structural gene fusions. Several different plant-expressible structural genes can be employed as enzymatic reporter genes. Successful expression has been reported for many light-inducible promoter/heterologous structural gene fusion constructs, for example, an *A. thaliana* Cab promoter fused to the promoterless chloramphenicol acetyltransferase (CAT) (An, (1987) Mol. Gen. Genet. 207:210–216) and a pea Cab promoter fused to the neomycin phosphotransferase II (NPT(II)) coding sequence (Simpson et al. (1986) Nature 323:551–554).

The vectors herein described employ the maize Cab promoter to control expression of an inserted DNA coding segment. The transcriptional regulatory sequences may be combined with a favored or optimized replication system for a predetermined host. For example, large quantities of a vector can be grown in prokaryotic systems prior to transforming a plant host. Other DNA sequences having restriction sites for gene insertion may be added to provide a vector for the regulated transcription and/or translation of the inserted genes in a given host. The principles for construction of a vector having proper orientation of the promoter and coding sequences with respect to each other are matters well known to those skilled in the art. In some situation it may be advantageous to join the promoter system to a desired structural gene and to introduce the resultant DNA construct directly into a host. Methods for such direct transfers include, but are not limited to, protoplast transformation, electroporation, direct injection of DNA into nuclei and co-transformation by calcium precipitation. Alternatively, recombinant vectors may be established as intermediate vectors, for example, by homologous recombination of a Ti plasmid in *Agrobacterium tumefaciens* (Rogers et al. (1986) Methods Enzymol. 118:627) and then cultures of the intermediate vector (e.g., recombinant *A. tumefaciens*) may be used to infect and transform different plant hosts (Rogers et al. (1986) supra). It has been demonstrated that Cab genes of wheat (Lamppa et al. (1985) Nature 316:750–752) and pea (Simpson et al. (1985) EMBO J. 4:2723–2729) are properly expressed and regulated in transformed tobacco plants. Other light-induced promoter/structural gene systems have also been expressed in petunia. Stable transformation of monocot cell lines has also been reported (Goodman et al. (1987) Science 236:48–54; Krens and Schilperoort (1984) in "Laboratory Procedures and Their Application," Vol. I of *Cell Culture and Somatic Cell Genetics of Plants*, L. K. Vasil (ed.) Academic Press, New York, pp. 522–534; Fromm et al. (1986) Nature 319:791).

The DNA of the present invention was isolated from the maize genomic library as the Cab AB1084 gene. The nucleotide sequence of the entire gene is given in FIGS. 2A and 2B. This constitutes the first report of an isolated Cab gene from maize. The DNA promoter/regulatory fragment of the present invention comprises 892 nucleotides upstream of the translation start site, the transcription start codon at position +1, a 'TATA' box at −35 and a 'CAAT' box at −90. In addition, there are specific sequences controlling gene expression in response to different genetic and environmental stimuli, for example, illumination, plant development, tissue specificity, etc.

Specific DNA sequences are tested for expected functionality as is well-known in the art. For example, sequences presumed to be responsible for light-inducibility may be deleted from the promoter fragment and the resultant construct shown to be light-insensitive; reinsertion of the deleted sequence or of a chemically synthesized or modified oligonucleotide equivalent sequence restores light-responsiveness (Morelli et al. (1985) Nature 315:200–204; Timko et al. (1985) Nature 318:579–582; Nagy et al. (1986) Phil. Trans. R. Soc. Lond. 314:493–500; Simpson et al. (1986) supra). In this way and for such reasons, the isolated Cab AB1084 promoter/regulatory fragment may sustain controlled and specific modifications without loss of promoter and/or regulatory functionality.

In general, the promoter/regulatory region is isolated as a restriction fragment which, either as an intact or a chemically modified fragment, is fused to a plant-expressible structural gene and then tested specifically for promoter and different regulatory functions. For example, in the present invention the promoter/regulatory fragment is isolated from the 4 kbp Cab AB1084 gene as an approximately 910 nucleotide EcoRI/NcoI fragment, the 3' end of which contains the translation start site and 15 additional nucleotide pairs. To ensure that the promoter fragment is devoid of the translation start codon, the 3' end of the promoter fragment is selectively digested with double-stranded exonuclease under controlled conditions to remove a desired number of nucleotide pairs. It is desirable to remove the Cab translation start codon so that translation of the inserted gene will commence at its own start site. The intact or chemically modified promoter fragment, after purification, is then inserted into an appropriate vector using linkers or homopolymer tailing to introduce desired restriction sites compatible with the remaining regions of the vector. In general, without undue experimentation, the promoter fragment may be manipulated with specific restriction enzymes and the resultant modified DNA fragment tested for promoter functions and compared to that of the intact promoter system.

Recombinant DNA constructs are useful as cloning vehicles for a structural gene of interest in a plant host under conditions which will allow the promoter and regulatory sequences to express the desired gene optimally. A wide variety of structural genes may be introduced into the subject DNA cloning vectors for the production of desired proteins, such as enzymes, hormones and the like. In addition, DNA constructs of this type can be used for the enhanced production of DNA derived from a particular gene, as well as for enhanced production of mRNA which can be used to produce cDNA. Such vectors carrying specific DNA sequences find wide application and are quite versatile; for example, they can be used for amplifications in bacteria as well as for expression in higher cells which allow for additional cellular functions. An advantage of utilizing higher eukaryotic recombinant systems to produce commercially medically and agriculturally desirable proteins is that they ensure correct post-translational modifications which may otherwise be difficult to duplicate in prokaryotic or lower eukaryotic hosts. In this invention, recombinant molecule comprising the maize Cab promoter/regulatory segment are tested in monocotyledonous and dicotyledonous plants.

The present invention also relates to the utilization of the maize Cab AB1084 gene promoter as a dark-regulated as well as a light-regulated promoter. Many photoresponsive genes exhibit approximately 100 fold enhancement in expression levels of certain genes (e.g., Cab and rbcS) in response to illumination. Recorded levels of constitutive Cab mRNA are consistently low in most plant species grown in the dark (Bennet et al. (1984) J. Cell. Biochem. 25:1–13; Nelson et al. (1984) J. Cell. Biol. 98:558–564). After a brief treatment with red light, a rapid increase in the amount of mRNA is induced and this level of enhancement can be suppressed by immediate far-red light treatment. This increase appears to be due to a phytochrome induced increase in the art of transcription, rather than to a change in stability of the transcript (Mosinger et al. (1985) Eur. J. Biochem. 147:137–142.

This generalized pattern of light-inducible gene expression in plants—low expression levels in the dark and significant enhancement of expression in the light—was compared to the differential expression reported for six individual genes from a maize Cab multigene family (Sheen and Bogorad (1986) supra). Only two of the six maize Cab genes studied matched the generalized pattern of photoregulated gene expression. Three of the six Cab genes did not show strong light stimulation of gene expression. These observations indicated that the regulation of gene expression was different for individual members of a multigene family and that not all Cab genes followed an all-or-nothing response to a light stimulus.

The Cab AB1084 promoter system of our invention functions actively in controlling and regulating transcription under both light and dark conditions. AB1084 mRNA makes up about 0.4% of the total mRNA pool in leaves of dark-grown plants, and may account for as much as 80% of the total Cab transcripts in dark leaves. The absolute amount of AB1084 mRNA (approximately 0.04 ng per µg of total cellular RNA) is unusually high in dark-grown maize leaves; this value corresponds to approximately 6% of the light induced levels. This means that one gene (AB1084 of this invention) functioning in darkness contributes about 6% to the total amount of Cab mRNA produced by all Cab genes operating under conditions of light. A contribution of 6% by one gene in a multigene situation is relatively substantial, as judged from the studies of Sheen and Bogorad (1986) supra on six maize Cab genes whose individual contributions to the total light induced transcription level ranged from 4% to 30%. It thus appears that the maize Cab gene AB1084 mRNA is unexpectedly abundant in maize leaves in the dark.

Figure 3A:
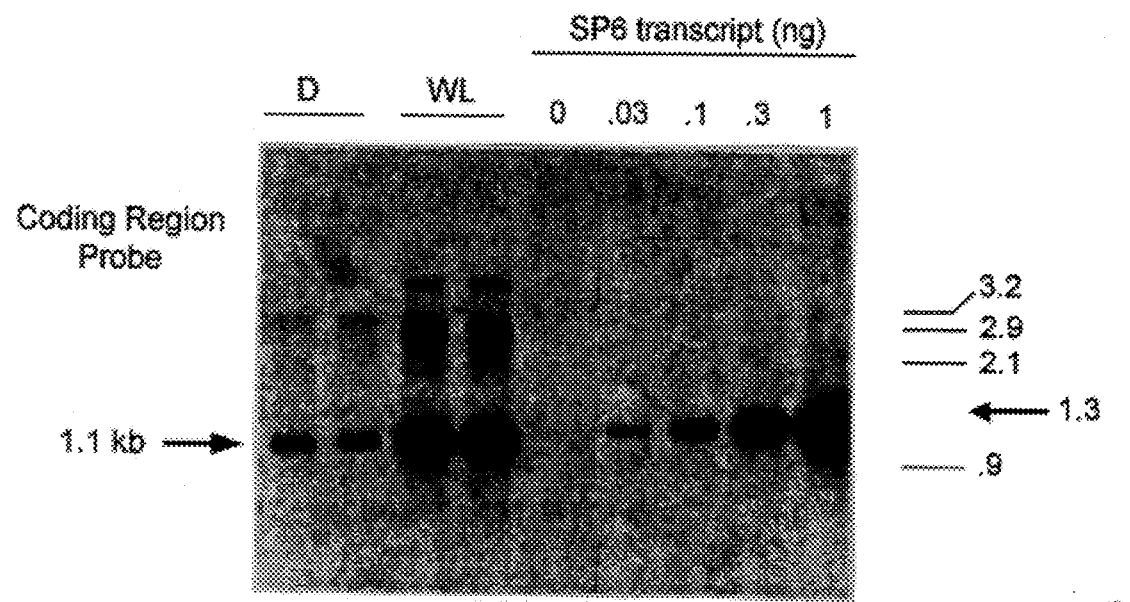
FIGS. 3A and 3B are is a Northern blot analysis of Cab mRNA in dark- and white-light treated seedlings. Total cell RNA (1 μg) from dark-grown (D) and 24-hour white-light (WL) treated eight-day-old seedlings was loaded in duplicate lanes as indicated. The right side of the gel contains in vitro transcribed SP6/Cab RNA (pSPCAB, HindIII cut template) which was included as a concentration standard for the hybridization signal. Parallel gels were run, blotted and hybridized with the probes indicated: (A) Coding region probe (ΔJ8/NcoI.
Figure 3B:
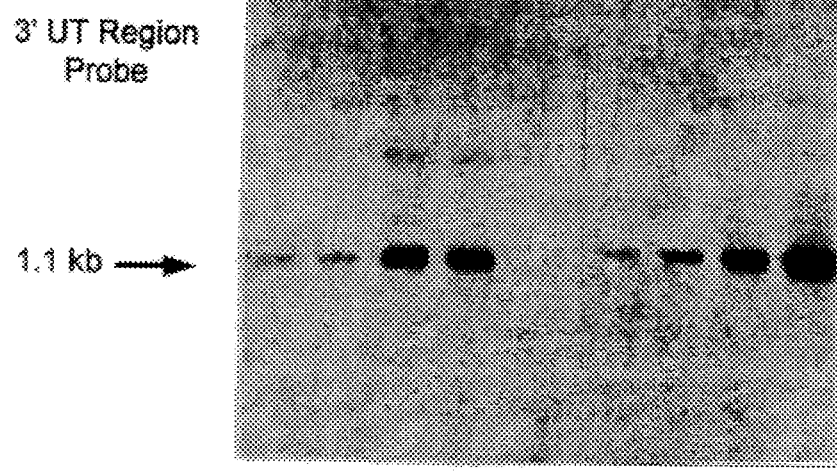

Twenty-four hours of white light treatment induced a 3- to 6-fold increase in AB1084 mRNA level, whereas the induction of total Cab mRNA by white light was 6- to 15-fold (see FIGS. 3A, 3B and Example 2). Again, individual genes are regulated to greater and lesser extents than the "average" gene determined with nonspecific coding region probes.

The 3- to 6-fold level of enhancement calculated for Cab AB1084 mRNA as a light/dark expression ratio reflects the high activity of our Cab gene under conditions of darkness. Previous studies (Lamppa et al. (1985) supra; Nelson et al. (1984) supra) documenting between 9- and 100-fold enhancement in light stimulated mRNA levels indicate that the dark regulated levels are barely detectable or very low, accounting for approximately 0.5% of the light induced levels (Nelson et al. (1984) supra). In out studies, higher levels of enhancement can be calculated, if the contribution by AB1084 expression in the dark is subtracted from the total Cab expression in the dark. Such calculation shows that the contribution by Cab genes other than AB1084 to dark regulated expression is approximately 1.5% of the light induced mRNA level and that, on this basis, the light induced enhancement of expression is from 40- to 65-fold. Comparable results were obtained by Timko et al. (1985) supra, who reported dark regulated expression levels of approximately 1% of the normal light regulated values in various chimeric pea rbcS promoter/structural gene fusions and, also, light/dark induction ratios of approximately 38. Thus, the presence of a promoter that is constitutively active under conditions of darkness influences significantly the calculated light/dark level of enhancement.

The Cab AB1084 promoter/regulatory system of this invention exhibits a pattern of expression that is differently regulated from that of other maize Cab genes. The fact that, in contrast to other maize Cab genes, this Cab promoter system functions actively under both light and dark conditions points to a specialized cellular role for the Cab AB1084 promoter in allowing an ambient level of Cab mRNA to be maintained in developing and mature plant leaves.

Production of a genetically modified plant expressing a foreign structural gene combines the specific teachings of the present disclosure with a variety of techniques and expedients known in the art. In most instances, alternative expedients exist for each stage of the overall process. The fundamental aspects of the invention are the nature and structure of the plant promoter/structural gene construct. The remaining steps to obtaining a genetically modified plant include transferring the recombinant molecule to a plant cell wherein it becomes stably integrated as part of the plant cell genome, techniques for in vitro culture and eventual regeneration into whole plants, which may include steps for selecting and detecting transformed plant cells and steps of transferring the introduced gene from the originally transformed strain into commercially accepted cultivars.

The following examples are offered by way of illustration and not by way of limitation.

EXAMPLES

Example 1

Isolation and Characterization of a Maize Cab Gene

A. Growth of Plants

Maize seed (*Zea mays*, inbred line B73 obtained from Jacques Seed Company or Pioneer Hybrid Seed Company) were germinated in wet vermiculite or sterile potting soil, and incubated at 25° C. Samples were grown in complete darkness from the start of germination (without green safelight) or in fluorescent white light (250 µE/m$^2$/sec at 400–700 nm) as indicated.

B. RNA Isolation

Leaves were harvested, frozen in liquid nitrogen and stored at −80° C. Total cell RNA was purified by guanidinium thiocyanate extraction and centrifugation through CsCl. Poly (A)$^+$ RNA was isolated from total cellular RNA by passage over a poly U-Sephadex (Bethesda Research Laboratories, Gaithersberg, Md.) column. Total or poly(A)$^+$ RNA were electrophoresed in 1.5% agarose gels containing 3% (wt/vol) formaldehyde. RNA was transferred to Gene Screen™ (DuPont) by capillary blotting using 25 mM sodium phosphate (pH 6.5).

C. cDNA Library Construction

Double-stranded cDNA synthesis from poly(A)$^+$ RNA, oligo (dc)-tailing of the double-stranded cDNA and annealing of oligo(dc)-tailed cDNA with oligo(dc)-tailed pBR322 were performed according to the procedures described by Hershey et al. (1984) Proc. Natl. Acad. Sci. 81:2332–2336. The annealed DNA was transformed into *E. coli* and plated directly onto nitrocellulose filters on L-agar plates containing tetracycline (15 µg/ml). Individual tetracycline resistant clones were grown up and DNA was prepared by a "miniprep" procedure (Maniatis et al. (1982) *Molecular Cloning, A Laboratory Manual*, Cold Spring Harbor Laboratory, Cold Spring Harbor, N.Y.). The DNA was spotted in duplicate on nitrocellulose membrane for use in a differential hybridization screen.

D. Identification of Cab cDNA $^{32}$P-cDNA probes were synthesized with reverse transcriptase from poly(A)$^+$ RNA from leaves of plants (day-5 post-germination) grown either in the dark or 3 hours after a pulse of red light (R3) (Hershey et al. (1984) supra). The cDNA library was screened for clones that gave different hybridization signals with the dark and R3 cDNA. Two clones, pAB1084 and pAB231, showed increased hybridization with the R3 probe. In addition, these two clones reacted with a light-inducible 1200 nucleotide transcript on Northern blot analysis and were shown by hybridization analysis to contain sequences homologous to the pea Cab gene clone AB80 (Cashmore (1984) Proc. Natl. Acad. Sci. 81:2960–2964).

E. Genomic Library Construction and Screening

DNA was isolated according to the method of Murray and Thompson (1980) Nucl. Acids Res. 8:4321–4325. DNA was partially digested with restriction enzyme Sau3a and cloned into the BamHI site of Charon 35 (Loenen and Blattner (1983) Gene 26:171–179) as described by Murray et al. (1984) Gene 30:237–240. A library of 2×10$^6$ pfu was screened for phage containing sequences homologous to the maize Cab cDNK clone pAB1084 by in situ plaque hybridization. One recombinant, λAB1084, containing a 10.3 kbp insert with homology to Cab was isolated (see. FIG. 1). The 4 kbp internal EcoRI fragment of λAB1084 contains the region of homology to pAB1084 and it was subcloned into pBR322 and M13mp18 (pAB41 and mCAB41, respectively) for use in making probes and for sequencing.

F. Cab Gene and Protein Sequence Analysis

For sequence analysis, the 4 kbp EcoRI fragment of AB1084 was subcloned in both orientations into the EcoRI site of M13mp18 (Yanisch-Perron et al. (1985) Gene 33:103–119). For each orientation, a series of overlapping Exonuclease III deletions was produced and cloned. The deletion clones were used for sequencing by the dideoxychain termination method (Biggin et al. (1983) Proc. Natl. Acad. Sci. 80:3963–3965) with an M13 "universal primer" (New England Biolabs). DNA sequence analyses were performed using programs provided by the University of Wisconsin Computer Group (Devereux et al. (1984) Nucl. Acid Res. 12:387–395).

The sequence of the entire polypeptide coding region, 5' and 3' untranslated regions, and several hundred bases of flanking DNA is reported for AB1084 in FIGS. 2A and 2B. The sequences of the two Cab cDNA clones are identical to each other and to the genomic clone λAB1084 (except for a single base change in one of the cDNAs at position 670 of FIG. 2B, which probably represents a reverse transcriptase error). The sequence of pAB1084 runs from position 428 to 1033 where it ends in a polyA tract (FIGS. 2A and 2B). As found for most of the Cab genes that have been analyzed, AB1084 does not contain an intron.

The derived amino acid sequence of the Cab gene is shown in FIG. 2 below the corresponding nucleotide sequence. Both the nucleotide and deduced amino acid sequences share extensive homology with the sequence of other published Cab genes. For example, in the 233 amino acid long mature protein region there is 83% nucleotide and 90% amino acid homology with a wheat Cab gene, 76% nucleotide and 94% amino acid homology with a pea Cab gene, and 92% nucleotide and 94% amino acid homology with a recently reported maize cDNA clone (Matsuoka et al. (1987) Nucl. Acids Res. 15:6302).

On the basis of comparison with other Cab proteins, the N-terminal 29 amino acids of the deduced amino acid sequence represents the transit peptide (Karlin-Newmann and Tobin (1986) EMBO J. 5:9–13). The amino acid sequence of the transit peptide in the recently published maize Cab cDNA clone is only 61% homologous to the transit peptide of AB1084. This is consistent with results from other species which indicate that the overall sequence in the transit peptide is less well conserved than in the mature Cab protein. In AB1084 the sequence of the transit peptide N- and C-termini does make a good match with the consensus sequence derived by Karlin-Newmann and Tobin (1986) supra, for transit peptides of Cab proteins from several species. There is a 9 out of 10 agreement at the N-terminus, and 5 out of 6 match at the transit/mature protein junction (FIGS. 2A and 2B).

G. Characterization of the Promoter and Other Flanking Regions

To delineate the transcribed sequences of the cloned gene, S1 nuclease mapping of the Cab mRNA was used as described by Weaver and Weissmann (1979) Nucl. Acid Res. 7:1175–1193. Probes for S1 nuclease mapping were made using either the 4 kbp internal EcoRI fragment of AB1084 (FIG. 1) subcloned into pBR322 (pAB41) or Exonuclease III deletion clones of the same EcoRI fragment in M13mp18 (FIG. 1).

The probe for S1 mapping of the 5' terminus of Cab mRNA was produced by end-labeling the NcoI sites in pAB41 with λ-$^{32}$P-ATP (New England Nuclear, NEN) and T4 polynucleotide kinase (New England Biolabs). After secondary digestion with EcoRI, the fragments were separated on a denaturing acrylamide gel, and a 900 bp fragment (FIG. 1) was isolated by electroelution.

For mapping the 3' mRNA termini, a single-stranded, uniformly labeled probe was produced by synthesizing complementary DNA from single strand M13 phage DNA of deletion clone ΔK20 (FIGS. 1, 2A and 2B) using universal M13 primer, large fragment of DNA polymerase I (Bethesda Research Labs, BRL) and α-$^{32}$P-dATP at 140 Ci/mmole (12 μM) as described by Myers et al. (1985) Nature 313:495–497) with the following modifications: After incubation with radioactive dATP for 45 min. at room temperature, unlabeled dATP was added to 150 μM and the reaction was allowed to proceed an additional 15 min. The DNA was ethanol precipitated with yeast tRNA as carrier and digested with NsiI. A single strand 265 nucleotide fragment (ΔK20/NsiI) was purified twice by denaturing (8M urea) acrylamide gel electrophoresis and electroelution, and was used immediately.

Hybridization and S1 nuclease digestion were performed as described by Carlson and Ross (1983) Cell 34:857–864, with some modifications. For 5' mapping, 2.0×10$^4$ cpm of the 900 bp 5'-$^{32}$P-NcoI/EcoRI fragment at 10$^6$ cpm/pmol was ethanol precipitated with 40 μg of total RNA from white-light grown maize leaves or with an equivalent amount of yeast tRNA. The probe/RNA pellet was resuspended in 40 μl of deionized formamide (100%), heated at 70° C. for 10 min., and 10 μl of concentrated buffer was added to make 80% formamide, 540 mM NaCl, 9 mM Tris (pH 7.4) and 10 mM EDTA. The samples were incubated at 50° C. for 15 hours. S1 nuclease (NEN) was added to a final concentration of 50 to 500 units/ml in 10 volumes of S1 buffer (280 mM NaCl, 50 mM sodium acetate, 4.5 mM ZnSO$_4$, pH 4.6, with 20 μg/ml sonicated, heat denatured salmon testes DNA), and the samples were incubated at 37° C. for 1 hour. The digestion reactions were terminated by the addition of 0.25 volumes of a solution containing 2.5M ammonium acetate and 50 mM EDTA, and one volume of isopropanol. After precipitation at −80° C., the samples were centrifuged, the pellets were washed with 70% ethanol, dried and resuspended in formamide containing bromphenol blue prior to heat denaturation and electrophoresis in 8% acrylamide gels containing 8M urea. After electrophoresis the gel was fixed in 10% acetic acid/10% methanol, dried and exposed to X-ray film at −80° C. with an intensifying screen (DuPont, Lightening Plus).

For 3' end mapping, $1 \times 10^4$ cpm of the 265 nucleotide single strand fragment ($\Delta$K20/NsiI) at $2.7 \times 10^7$ cpm/pmol was hybridized with tRNA, 2 ng of Sp6/Cab in vitro synthesized transcripts, or 2 μg of total RNA from white light treated maize leaves. Hybridization and S1 nuclease conditions were as above, except that hybridizations were done in 30 μl of hybridization buffer with 50% formamide at 45° C. for 12 hours. S1 nuclease digestion was at 37° C. for 30 min. with 50 units/ml nuclease.

When the 5' terminus probe (5'-end labeled at the NcoI site, 15 nucleotides downstream from the start codon, FIGS. 1, 2A and 2B) was hybridized to RNA from white light-grown maize leaves and treated with S1 nuclease, a 70 nucleotide fragment was protected. The S1 nuclease treatment did not yield a single protected fragment. Rather, three major fragments differing by one nucleotide each were protected. This is in agreement with published results of S1 mapping experiments with other mRNAs. Increasing the concentration of enzyme shifts the ratio of the amount of each band. The actual CAP site is likely to be at one of these three sites and the A was selected as +1 (FIGS. 2A and 2B) because it represents the most resistant to S1 nuclease digestion products. This result localizes the 5' terminus (i.e., the presumptive CAP site) of the AB1084 mRNA to 52–54 nucleotides upstream of the translation start site codon. The 5' flanking region contains the sequences TATTTA at position −35 and CCAAT at −90 (FIG. 2). These sequences are often found in the 5' flanking region of eukaryotic genes and appear to be essential for efficient transcription initiation of those genes (Myers et al. (1984) Nature 232:613–618).

Messenger RNA derived from individual Cab genes in petunia contain multiple polyA addition sites (Dean et al. (1986) Nucl. Acid Res. 14:2229–2240). Evidence for multiple 3' termini in maize Cab mRNA was obtained by S1 mapping. The 3' termini were first mapped using 3'-end labeled probes. These probes, labeled at an XhoI site (position 759) or Hpa2 site (position 841), indicated multiple 3' ends in the region. 170–230 nucleotides downstream from the translation stop codon. These sites are in the region of the polyA tract found in the sequence of the cDNA clone pAB1084, which maps to 192 nucleotides downstream of the stop codon (FIGS. 2A and 2B).

Further experiments were performed to more precisely map the 3' termini. No convenient restriction sites are present for making end-labeled probes closer to the termini; therefore, a uniformly labeled probe was made by synthesizing complementary strands of the deletion clone $\Delta$K20 in M13. This clone ends approximately 300 nucleotides downstream from the stop codon. The template/complement was digested with NsiI and a 265 nucleotide single strand fragment was isolated from a denaturing acrylamide gel (FIG. 1).

When this 3' terminus probe was used in an S1 nuclease protection experiment, four groups of protected fragments were produced (FIGS. 2A and 2B). These fragments map 190–240 nucleotides downstream of the stop codon. One group of fragments (A) map to the region identified as the poly A addition site of cDNA clone pAB1084. Each of the other sets of fragments (B–D) represent polyA addition sites. downstream of site A. It is unlikely that any of these protected fragments are the result of hybridization of the probe from Cab gene AB1084 with mRNA from the other Cab genes since a probe containing these sequences only reacts with DNA from the homologous gene on genomic Southern blots.

The DNA sequences in the region of the 3' termini is very A+T-rich. Therefore, it is theoretically possible that some of the fragments generated by S1 nuclease treatment are the result of digestion of regions of "breathing" in the RNA/DNA duplex (Maquat et al., (1981) Cell 27:543–553). This possibility was tested by using in vitro transcribed RNA from the cloned Cab gene in parallel S1 nuclease digests. In vitro transcribed SP6/Cab RNA with two different 3' termini (EcoRV or HindIII; FIGS. 1 and 2) protected the predicted sequences of the probes. No extra bands resulting form digestion at internal sites were detected. These data support the conclusion that transcripts from the maize Cab gene AB1084 can have different 3' termini.

Dean and co-workers (1986, supra) showed that the polyA addition signal in plant genes is less well conserved than the sequence AATAAA found 10–33 nucleotides upstream of the polyA site in animal genes. They have derived a consensus sequence for plant polyA addition signals based on 15 cloned cDNAs. In the 3' untranslated region of AB1084 there are hexanucleotide sequences that fit this consensus. The sequence AACCAT ending 163 nucleotidase past the stop codon precedes the A, B and C termini by 29–53 nucleotides. The sequence ATTAAT (221 nucleotides from the stop codon) precedes the D terminus by 12 nucleotides (FIGS. 2A and 2B).

H. Northern and Southern Blot Analysis

The probes used for northern and Southern blot analysis were single stranded fragments synthesized as for the 3' S1 mapping probe. The coding region was synthesized from clone $\Delta$J8, cut at NcoI, and a 720 nucleotide fragment was purified ($\Delta$J8/NcoI, $8 \times 10^7$ cpm/pmol, FIG. 1). The 3' untranslated region probe was synthesized from deletion clone $\Delta$K20, cut at NciI, and a 350 nucleotide fragment was purified ($\Delta$K20/NciI, $2 \times 10^7$ cpm/pmol, FIG. 1).

RNA samples were denatured, run on a 1% (w/v) agarose gel containing 2.5M formaldehyde, blotted to nylon membrane (Gene Screen, NEN) in 25 mM phosphate buffer (pH 6.8) and hybridized to $^{32}$P probes as described by Lissemore et al. (1987) Plant Mol. Biol. 8:485–496. Prehybridization and hybridization buffers were made up with either 50% (v/v) or 30% (v/v) formamide as indicated. Hybridizations were done overnight at 42° C. Membranes were first washed in 2× SSC (150 mM NaCl and 15 mM Na citrate), 5 mM EDTA, 25 mM NaPO$_4$ (pH 6.8), 1.5 mM Na pyrophosphate, and 0.5% (w/v) sodium dodecyl sulfate (SDS) at room temperature and then further washed with the same buffer containing 2×, 0.5× or 0.1× SSC at 42° C. or 65° C. as indicated. Autoradiography was at −80° C. with an intensifying screen.

DNA for Southern blot analysis was digested to completion with EcoRI or HindIII and electrophoresed in a 0.8% (w/v) agarose gel. The gel was treated sequentially with 0.25M HCl, 0.5M NaOH and 1.0M Tris, 1.5M NaCl and blotted to Gene Screen Plus membrane (NEN) in 20× SSC. Prehybridization and hybridization conditions were performed as for northern blots and as indicated.

I. SP6 Polymerase Transcription

The Cab mRNA region and some flanking DNA from deletion clone $\Delta$K20 were subcloned from pAB41 into the polylinker of pSP19. To generate SP6/Cab mRNA, this plasmid, called pSPCAB, was linearized with either EcoRV, which cuts 212 nucleotides beyond the translation stop codon, or HindIII, which cuts in the pSP19 polylinker beyond the Cab insert and results in an RNA containing 305 nucleotides beyond the stop codon of the Cab gene plus additional sequences from the M13 clone and the pSP19 polylinker (FIG. 1). Ten µg of linearized plasmid was transcribed in 100 µl final volume with 30 units SP6 polymerase (Promega Biotec) in 40 mM Tris (pH 7.5), 6 mM MgCl$_2$, 2 mM spermidine-HCl, 10 mM DTT, 50 µg/ml BSA (nuclease-free, BRL), 0.5 mM each of ATP, CTP, GTP and UTP at 40° C. for 1 hour. After transcription the samples were extracted with phenol:chloroform:isoamyl alcohol (100:48:2), ethanol precipitated and resuspended in 10 mM Tris (pH 7.5), 0.1 mM EDTA. Concentrated LiCl was added to make 2M, the samples were kept overnight at 4° C., centrifuged and the pellet was resuspended and ethanol precipitated. This LiCl precipitation step removed most of the DNA and the resulting RNA contained less than 5% DNA. The amount of RNA recovered was determined by absorbance at 260 nm with an absorbance of 1.0 given as 42 µg/ml. These in vitro transcribed RNAs (SP6/Cab RNA) were used as controls for S1 nuclease digestions and as concentration standards for quantitating the amount of Cab mRNA detected on northern blots.

Example 2

Maize Cab Gene Expression

A. Probe Specificity for Total and Specific Cab Genes

Two different probes were made from subclones of AB1084. One probe was derived entirely from the coding region of the gene (ΔJ8/NcoI) and should react, when used at low stringency, with sequences common to all Cab genes. The second probe contains sequences from the 3' untranslated region of the mRNA (ΔK20/NciI) and is specific for AB1084 as demonstrated by hybridization analysis.

The specificity of each probe was tested by Southern blot hybridization of maize genomic DNA. The coding region probe, ΔJ8/NcoI, reacts with multiple bands on the blot. This result indicates that the probe cross-hybridizes to many Cab genes and, therefore, it should be useful for analyzing total Cab mRNA. In contrast, even under low stringency hybridization conditions (30% formamide, 42° C.), the 3' untranslated region probe, ΔK20/NciI, is specific for AB1084. It reacts with only one size DNA, a 4.0 kbp EcoRI fragment, which is the same as the EcoRI fragment that contains the Cab gene in λAB1084 (FIG. 1). During northern blot analysis with ΔJ8/NcoI, hybridization and wash conditions were intentionally set to allow cross-hybridization with other Cab mRNA, while ΔK20/NciI was used under much more stringent conditions to ensure that the probe reacted only with AB1084 mRNA.

B. Light Regulation of Transcription

Nelson and co-workers (1984) J. Cell Biol. 98:558–564 have shown that the Cab mRNA level in maize increases dramatically between seven and nine days post germination and that most of the increase is light-dependent. We have measured the effect of white light treatment on the amount of both total Cab mRNA and AB1084 mRNA 8 days after germination. In vitro transcribed SP6/Cab mRNA was used as a concentration standard for determining the relative amounts of Cab mRNA.

In RNA from both dark-grown and white light-treated maize leaves the predominant size RNA detected was about 1100 nucleotides as shown in FIG. 3, panels A and B. This size matches well with the predicted size of the Cab mRNA based on S1 mapping of the 5' and 3' termini (1032–1072 nucleotides from the CAP site to the polyA addition sites) and with the additional nucleotides provided by the polyA tail (FIGS. 1, 2A and 2B). The 1239 nucleotide SP6/Cab RNA also migrates as expected (FIG. 1).

The amount of either total Cab mRNA or AB1084 mRNA in the dark or white light treated samples was quantitated by densitometer scans of the bands and comparison with the SP6/Cab RNA signals. In the experiment shown in FIG. 3, there is a 13-fold increase in Cab mRNA following a 24 hour white light treatment as detected by the coding region probe (panel A, D vs. WL). In contrast, there was only a 6-fold increase in AB1084 mRNA with a white light treatment (based on results using the 3' untranslated region probe, ΔK20/NciI (panel B)). This trend was seen in repeated experiments, including those in which the polyA$^+$ fraction of the cell RNA was tested. The range for the white light increase in mRNA abundance was 6- to 15-fold for total Cab mRNA and 3- to 6-fold for AB1084. If the coding region probe made form the AB1084 gene does not efficiently hybridize to Cab mRNA from all the different Cab genes, then it is possible that these results are an underestimate of the induction of total Cab mRNA.

This possibility is suggested by the results of genomic Southern blot hybridization in which hybridization signals differ between the fragments detected. Differential hybridization efficiency among the Cab gene sequence may also explain why the results in FIGS. 3A and 3B differ quantitatively from those of Nelson et al. (1984) supra who report a 100- to 200-fold increase in response to a similar situation.

C. Quantitation of the Amount of Expression in the Dark

Quantitation of the amount of AB1084 mRNA in the dark and its increase in response to light treatment are based on homologous hybridization with a gene-specific probe and comparison with known amounts of the SP6/CAB RNA. Therefore, the calculation of the amount of AB1084 mRNA is not complicated by the question of hybridization efficiency. There are two main conclusions of the quantitations made from experiments such as in FIGS. 3A and 3B. First, as indicated by Sheen and Bogorad (1986) Proc. Natl. Acad. Sci. 83:7811–7815, there are differences in the expression of maize Cab genes in response to light treatment. AB1084 represents a gene with only a moderate increase in its mRNA level in response to light treatment. The 3- to 6-fold increase in AB1084 mRNA is lower than the total Cab mRNA induction detected with the, coding region probe, as in FIGS. 3A and 3B, and it appears to be lower than the mRNA(s) detected in the experiments of Nelson et al. (1984), supra, with a maize Cab cDNA probe.

Second, the absolute amount of AB1084 mRNA is high in dark-grown leaves and may represent the majority of Cab mRNA in the dark. On the basis of estimates of total Cab mRNA in maize leaves (FIG. 3), AB1084 may account for as much as 80% of the total Cab mRNA in the dark (0.04 ng AB1084 vs. 0.05 ng total Cab mRNA per µg of total RNA).

It is clear that the absolute amount of AB1084 mRNA is quite high in maize leaves. In the experiment shown in FIG. 3, the amount of AB1084 Cab mRNA present in dark-grown maize leaves is approximately 0.04 ng/µg of total cellular RNA. This is equivalent to 0.4% of the polyA$^+$ RNA in this tissue. It thus appears that the maize Cab gene AB1084 promoter is very active in maize leaves in the dark.

Phytochrome Mediation of Expression

Since AB1084 is expressed at high levels in the dark and is only moderately inducible by white light treatment, it was not certain if AB1084 is actually a phytochrome-responsive gene. To establish whether the AB1084 response was phytochrome-mediated, the responsiveness of AB1084 to red light and the far-red light reversability of red light inductions (Thompson et al. (1985) Bioassays 3:153–159) were tested. RNA samples similar to those used for cDNA production were analyzed by blot hybridization with the AB1084 gene-specific probe (ΔK20/NciI). In fact, AB1084 mRNA was easily detected in the dark. The induction of AB1084 by a pulse of red light was low (approximately three fold) but was reversible by far-red light to the level of mRNA following a far-red light treatment alone. Thus, the level of AB1084 mRNA is regulated by phytochrome.

Example 3

Construction of a Recombinant Molecule Comprising the Maize Cab Promoter and a Structural Gene A. Promoter Isolation The promoter/regulatory region of the maize Cab gene AB1084 was isolated from the 4 kbp internal EcoRI fragment of λAB1084 subcloned into pBR322 (pAB41) by digestion with NcoI, followed by a secondary digestion with EcoRI. This EcoRI/NcoI fragment, spanning nucleotides −840 to +70, includes 15 nucleotides downstream from the translation start site. The ATG start codon in addition to the nucleotides downstream of it are selectively removed using controlled exonuclease digestion. An approximately 892 nucleotide deletion fragment is isolated by electroelution from a denaturing acrylamide gel. This upstream fragment comprises the promoter and regulatory sequences located 5' to the coding region of the maize Cab gene AB1084 up to position −840 (FIG. 1).

B. Recombination of Cab Promoter with Structural Gene

The isolated Cab promoter fragment is ligated to BamHI linkers and cloned as EcoRI/BamHI fragments into pUC9. These are ligated directly to an octopine synthase (ocs) cassette fragment (Herrera-Estrella et al. (1983) Nature 303:209–213) to create transcriptional fusions which can then be cloned into pMUC9 as PstI/SmaI fragments. This cassette fragment places an ocs coding sequence lacking any promoter but containing 3' sequences to an RsaI site 12 bp 3' to the polyA site between the convenient restriction sites BamHI and HindIII.

The sequences at the 5' end of the Cab gene promoter are shown in FIGS. 2A and 2B. The transcriptional fusion retains the 5' untranslated sequences. After construction of these fusions the structure at the fusion junction is confirmed by DNA sequencing.

C. Expression of Chimeric Genes into Plants

The modified Ti plasmid pGV3850kanR was constructed to introduce chimeric genes into plants (Zambryski et al. (1983) EMBO J. 2:2143–2150). This plasmid carries the nopaline synthase gene which can be used in addition to kanamycin resistance to screen for transformation of plant cells.

The Cab/ocs fusions are introduced into pGV3850 as described by van. Haute et al. (1983) EMBO J. 2:411–418. Agrobacterium transconjugates carrying co-integrates between pGV3850 and the Cab/ocs fusions were selected by plating in medium containing kanamycin and were used to infect both monocot and dicot plant specimens (Fraley et al. (1983) Proc. Natl. Acad. Sci. 80:4803–4807; Horsch et al. (1985) Science 227:1229–1231). Transformed tissue cells are selected by kanamycin resistance while cells from transformed shoots are verified by assaying for nopaline synthase activity (Otten et al., (1978) Biochim. Biophys. Acta 527:497–500). The presence of chimeric mRNA in transformed plants is determined by hybridizing the mRNA extracted from the plant with radioactive octopine synthase sequences (Otten et al. (1978), supra).

D. Light Regulation of Expression of Chimeric Genes

To determine whether the presence of the Cab upstream regulatory sequences could influence expression of the Cab/ocs construct, transgenic plants are examined for light inducibility of ocs activity. Plants are grown for 5 days in complete darkness, the level of octopine synthase activity is determined and they are then placed in continuous light conditions for 4 days after which octopine synthase activity in leaves of the same size and position on the plant is again measured. Alternatively, transformed plants are divided in two groups. One group of these plants is kept in light while the other group is kept in darkness for 5 days. Leaf extracts containing equal amounts of protein are then assayed for octopine synthase activity or extracted for hybridization analysis. To confirm that the observed light inducibility of ocs under control of the Cab promoter fragment in transgenic plants reflects changes in the level of steady state mRNA, total RNA is extracted from the pooled leaves of either light or dark-grown transgenic plants. The higher level of ocs mRNA (determined by blot-hybridization) in leaves of light-grown transgenic plants than in those grown in the dark, demonstrates that the presence of the Cab upstream sequences confers light inducible properties on the transcription of the ocs gene.

We claim:

1. A recombinant DNA molecule comprising:

(a) a dark- and light-active Cab promoter/regulatory system which cross-hybridizes with the Cab AB1084 promoter/regulatory system under stringent conditions, and wherein said promoter/regulatory system
   (i) functions to direct the expression of a structural gene under its control during conditions of darkness and
   (ii) is stimulated to direct enhanced expression of said structural gene under light conditions, and (b) a heterologous plant-expressible structural gene wherein said structural gene is placed under the regulatory control of said plant promoter/regulatory system.

2. The recombinant molecule of claim 1 wherein said Cab promoter/regulatory system is a subsequence derived from the Cab AB1048 promoter/regulatory system.

3. The recombinant molecule of claim 1 wherein said Cab promoter/regulatory system comprises the nucleotide sequence of FIG. 2, from about nucleotide −840 to about nucleotide +1.

4. The recombinant molecule of claim 1 wherein said plant-expressible structural gene is a photoregulated gene.

* * * * *

UNITED STATES PATENT AND TRADEMARK OFFICE
CERTIFICATE OF CORRECTION

PATENT NO. : 5,656,496

DATED : August 12, 1997

INVENTOR(S) : Peter H. Quail, Thomas D. Sullivan and Alan H. Christensen

Page 1 of 2

It is certified that error appears in the above-identified patent and that said Letters Patent is hereby corrected as shown below:

Column 1, line 50: "it has-been" should read --it has been--.

Column 2, line 1: "chlorophylis" should read --chlorophylls--;

line 23: "a cab gene" should read --a Cab gene--.

Column 3, line 67: "core Sequence" should read --core sequence--.

Column 5, line 51: "FIGS. 3A and 3B are is a" should read --Figure 3A and 3B are a--.

Column 7, line 7: "vital" should read --viral--;

line 47: "nopeline" should read --nopaline--.

Column 10, line 50: "amplifications" should read --amplification--;

lines 57-58: "molecule" should read --molecules--.

Column 11, line 56: "In out" should read --In our--.

Column 13, lines 38-39: "The deletion" should read --These deletion--;

line 58: "FIG 2 below" should read --Figure 2A and 2B below--.

Column 14, line 29: "with $\lambda$-$^{32}$P-ATP" should read --with $\gamma$-$^{32}$P-ATP--

UNITED STATES PATENT AND TRADEMARK OFFICE
CERTIFICATE OF CORRECTION

PATENT NO. : 5,656,496
DATED : August 12, 1997
INVENTOR(S) : Peter H. Quail, Thomas D. Sullivan and Alan H. Christensen It is certified that error appears in the above-identified patent and that said Letters Patent is hereby corrected as shown below:

Column 15, line 36: "(FIG 2)." should read --(Figs. 2A and 2B).--;

line 47: "region. 170-230" should read --region 170-230--.

Column 16, line 1: "addition sites." should read --addition sites--;

line 9: "some 0f" should read --some of--.

Column 17, line 4: "containing 305" should read --containing 305--.

Column 18, line 45: "with the, coding" should read --with the coding--.

Column 19, line 56: "van. Haute et al." should read --van Haute et al.--.

Column 20, line 51 (claim 2): "Cab AB1048" should read --Cab AB1084--.

Signed and Sealed this

Seventeenth Day of February, 1998

Attest:

BRUCE LEHMAN

Attesting Officer

Commissioner of Patents and Trademarks